US008207080B2

(12) United States Patent
Millet et al.

(10) Patent No.: US 8,207,080 B2
(45) Date of Patent: Jun. 26, 2012

(54) PREPARING A COMPOUND COMPRISING A COMBINATION OF TWO CRYSTAL PHASES

(75) Inventors: Jean-Marc Millet, Lyons (FR); Phillippe Lacorre, Coulaines (FR); Quyen Huynh, Danang (VN)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 666 days.

(21) Appl. No.: 12/279,420

(22) PCT Filed: Feb. 14, 2007

(86) PCT No.: PCT/FR2007/000260
§ 371 (c)(1), (2), (4) Date: Oct. 28, 2008

(87) PCT Pub. No.: WO2007/093702
PCT Pub. Date: Aug. 23, 2007

(65) Prior Publication Data
US 2009/0171118 A1   Jul. 2, 2009

(30) Foreign Application Priority Data
Feb. 14, 2006 (FR) ..................... 06 01284

(51) Int. Cl.
*B01J 27/00* (2006.01)
*B01J 27/198* (2006.01)
*B01J 27/188* (2006.01)
*B01J 27/19* (2006.01)
*B01J 27/192* (2006.01)
*B01J 27/185* (2006.01)

(52) U.S. Cl. ........ 502/208; 502/209; 502/210; 502/211; 502/212; 502/213

(58) Field of Classification Search ........... 502/208–213
See application file for complete search history.

(56) References Cited

U.S. PATENT DOCUMENTS

| 5,138,100 | A | 8/1992 | Matsura | |
|---|---|---|---|---|
| 6,476,259 | B2* | 11/2002 | Kase et al. | 562/532 |
| 6,919,472 | B2* | 7/2005 | Hazin et al. | 558/321 |
| 7,009,075 | B2* | 3/2006 | Hazin | 562/549 |

FOREIGN PATENT DOCUMENTS

| EP | 0418657 | 3/1991 |
|---|---|---|
| FR | 2756499 | 6/1998 |
| JP | 09-299803 | * 11/1997 |
| JP | 09299803 | 11/1997 |

OTHER PUBLICATIONS

"Specific insight of active sites in Cs2TexVyPMo12O40 catalysts efficient for selective oxidation of isobutane by operando resonance Raman spectroscopy," Stephane Loridant et al. Catalysis Today 155 (2010), pp. 214-222.*

* cited by examiner

*Primary Examiner* — Patricia L Hailey
(74) *Attorney, Agent, or Firm* — B. Aaron Schulman, Esq.; Stites & Harbison, PLLC

(57) ABSTRACT

The invention concerns a compound comprising a combination of two crystal phases. The first crystal phase corresponds to the formula: $A_aE_bV_cMo_dP_eO_fH_g$ wherein A is an alkali-metal; E is Te, Sb or Bi; and $0 \leq a \leq 3$, $0 < b \leq 3$, $0 \leq c \leq 3$, $0 < d \leq 13$, $0 < e \leq 2$, $0 \leq g \leq 3$. The second crystal phase corresponds to the formula $Z_gMo_hX_iO_j$ wherein: Z is selected among trivalent rare earths; X is selected among the elements V, Ga, Fe, Bi, Ce, Ti, Sb, Mn, Zn, Te; and $0 < g \leq 3$, $0 \leq h \leq 3$, $0 \leq i \leq 1$. The indices f and j represent the number of oxygen atoms required for satisfying the relative valency and atomic proportions of the elements present. The invention also concerns the method for preparing said compound, and its use in particular as catalyst for oxidizing alkanes.

25 Claims, 6 Drawing Sheets

PREPARING A COMPOUND COMPRISING A COMBINATION OF TWO CRYSTAL PHASES

The present invention relates to a compound comprising a combination of two crystal phases, one crystal phase being of the phosphomolybdic type, as well as to a process for its preparation and to several uses of the compound.

The compound according to the invention is intended more particularly for catalysing certain alkane oxidation reactions, especially the oxidation of isobutane to give methacrylic acid and methacrolein, which results in the formation of methyl methacrylate.

For obtaining methacrylic acid and methacrolein by oxidation of isobutane there are known, from the two publications mentioned hereinbelow, catalysts comprising two phases, in which one of the two phases is of the phosphomolybdic type.

In the publication of Q. Deng et al., J. Mol. Catal. A, 229, (2005) 165, the compound used as a catalyst is constituted by a phospho(arsenio)molybdic acid phase and a phase based on ferrous iron orthophosphate. In the two phases, part of the phosphorus must be replaced by arsenic. This catalyst therefore contains a large amount of arsenic, the toxicity of which limits the industrial use of the catalyst.

The publication of T. Ushikobo, Catalysis Today, 78, (2003) 79-84 describes a catalyst comprising a first phase formed of a heteropolyacid of the formula ($PMo_{11}VO_{40}$) and a second phase constituted by a tantalum oxide $Ta_2O_5$ previously treated with sulfuric acid. This catalyst has relatively low productivity, of the order of $30 \, g \cdot kg^{-1}_{cata} \cdot h^{-1}$. In addition, the stability of sulfated oxides over time is not very satisfactory, and the selectivity of the catalyst for methacrylic acid relative to methacrolein is low.

The object of the invention is to propose a compound which can be used as a catalyst and which does not have the disadvantages mentioned above, that is to say a compound which does not contain toxic elements and which has catalytic properties that are stable over time.

According to a first aspect, the invention relates to a compound comprising a combination of two crystal phases. The first crystal phase is of the phosphomolybdic type and corresponds to formula (1):

$$A_a E_b V_c Mo_d P_e O_f H_g \qquad (1)$$

in which:
A is an alkali metal;
E is selected from the elements Te, Sb and Bi, preferably Te and Bi;
the indices a, b, c, d, e, g are such that: $0 \leq a \leq 3$, $0 < b \leq 3$, $0 \leq c \leq 3$, $0 < d \leq 13$, $0 < e \leq 2$, $0 \leq g \leq 3$, and f represents the number of oxygen atoms necessary to satisfy the valence and the relative atomic proportions of the elements that are present.

According to a preferred embodiment, the alkali metal A is cesium.

The element E is preferably tellurium.
The second crystal phase corresponds to formula (2):

$$Z_g Mo_h X_i O_j \qquad (2)$$

in which:
Z is selected from the trivalent rare earths;
X is selected from the elements V, Ga, Fe, Bi, Ce, Ti, Sb, Mn, Zn, Te, preferably V, Ga, Fe, Bi, Ce, Ti, Mn, Zn, Te;
the indices g, h and i are such that: $0 < g \leq 3$, $0 \leq h \leq 3$, $0 \leq i \leq 1$, and j represents the number of oxygen atoms necessary to satisfy the valence and the relative atomic proportions of the elements that are present.

Advantageously, the first and second crystal phases do not comprise a Sb atom, which is highly toxic, thus allowing the compound to be used more readily on an industrial scale.

According to a preferred embodiment, the element Z represents lanthanum.

Likewise according to a preferred embodiment, the element X is vanadium.

According to an advantageous embodiment, the proportion of the second crystal phase is less than or equal to 50% by weight, based on the total weight of the compound.

The first crystal phase can correspond to the formula $Cs_2Te_{0.3}V_{0.1}H_{0.2}PMo_{12}O_{40.4}$.

The second crystal phase can correspond to the formula $La_2Mo_2O_9$ or to the formula $La_2Mo_{1.9}V_{0.1}O_{8.95}$, vanadium having replaced part of the molybdenum as compared with the preceding formula.

As examples of compounds according to the invention there may be mentioned those formed by a combination of a first crystal phase of the formula $Cs_2Te_{0.3}V_{0.1}H_{0.2}PMo_{12}O_{40.4}$ and a second crystal phase of the formula $La_2Mo_2O_9$, and by a combination of a first crystal phase of the formula $Cs_2Te_{0.3}V_{0.1}H_{0.2}PMo_{12}O_{40.4}$ and a second crystal phase of the formula $La_2Mo_{1.9}V_{0.1}O_{8.95}$.

In general, the process for the preparation of a compound according to the invention comprises the following steps:
synthesis of the first crystal phase in the form of a first powder;
synthesis of the second crystal phase in the form of a second powder;
mixing of said first and second powders by grinding.

This process has the advantage not only that it permits great flexibility in terms of the experimental conditions employed, since each phase is prepared separately, its formula thus being readily adaptable to the application in question, but also that it is simple to carry out, because final mixing of the two phases is effected by simple mechanical mixing of the powders.

The synthesis of the first crystal phase can comprise the following successive steps:
preparation of an aqueous solution comprising phosphomolybdic acid and a compound of the element E;
mixing of said aqueous solution with an aqueous solution comprising a salt of the element A;
precipitation, drying and calcination of said mixture in order to obtain a solid phase;
mixing of said solid with a toluene solution comprising a compound of vanadium;
filtration and drying at ambient temperature.

Among the compounds of the element E there may be mentioned the acids of the element E, such as telluric acid, the chlorides or the alkoxides of the element E.

Among the salts of the element A there may be mentioned the carbonates or the nitrates. Very particular preference is given to cesium carbonate.

Among the compounds of vanadium there may be mentioned vanadium oxide or vanadium acetylacetonate.

The synthesis of the second crystal phase can comprise the following successive steps:
mixing, by grinding, of molybdenum oxide $MoO_3$ in the solid state and an oxide of the element Z in the solid state;
heating of said mixture to a temperature of the order of 500° C.;
carrying out successive operations of annealing said mixture at a temperature greater than 500° C. until the end product is obtained in powder form.

When the element Z represents La, the annealing temperature is approximately from 850° C. to 960° C. The oxide used is then $La_2O_3$.

When it is desired to obtain a second crystal phase of formula (2) that comprises an element X, that is to say in which the index i is other than 0, part of the molybdenum oxide is replaced by a compound of the element X. If X represents vanadium, the compound used can be vanadium oxide or ammonium vanadate.

A compound according to the invention is advantageously used as a catalyst for the oxidation of alkanes, especially isobutane, propane, pentane. It can also advantageously be used as a catalyst for the oxidation of isobutene and methacrolein to give methacrylic acid.

The compound according to the invention is particularly efficient as a catalyst for the oxidation of isobutane to give methacrylic acid and methacrolein, as is described in the examples hereinbelow. The preparation of methacrylic acid and methacrolein starting from isobutane comprises passing a gaseous mixture comprising isobutane and water, and optionally an inert gas and/or molecular oxygen, over a compound according to the invention. The tests which have been carried out show that a synergy effect took place between the two phases of the compound according to the invention, the observed activity not corresponding to the simple sum of the activities of the pure phases. This synergy effect between the two phases is due to the fact that the second crystal phase acts not only as substrate but also as co-catalyst by selectively converting isobutane into isobutene, the resulting isobutene then being selectively converted into methacrylic acid on the phosphomolybdic compound forming the first phase.

The present invention is illustrated hereinbelow by concrete examples, but it is not limited thereto. Examples 1 and 2 describe the preparation and characterization of compounds according to the invention, as well as the study of their catalytic properties in the oxidation reaction of isobutane to give methacrylic acid and methacrolein.

Various methods have been used to characterize the compounds. These characterization methods are described hereinbelow.

BRIEF DESCRIPTION OF THE DRAWINGS

(FIG. 5a) and 369° C. (FIG. 5b) as a function of the content by weight of lanthanum molybdate (denoted LM, in %).

CHEMICAL ANALYSIS

For the chemical analysis of the compounds, cesium was analyzed by air-acetylene flame atomic emission (on a spectrometer marketed by Perkin-Elmer) and the other elements were analyzed by ICP plasma (inductively coupled plasma) atomic emission on a spectrometer marketed by Spectro. The wavelengths used for the analysis are shown in Table 1.

TABLE 1

|  | P | Mo | V | Te | Cs |
|---|---|---|---|---|---|
| Wavelength (nm) | 353.565 | 281.61 | 311.07 | 214.28 | 852.3 |

Measurement of Specific Surface Area

The specific surface areas were measured by the BET method. The quantity of nitrogen adsorbed at −196° C. was measured by volumetry. Before each measurement, the samples were desorbed for 2 hours under a secondary vacuum at 250° C.

Infra-Red Spectrometry

The infra-red spectra were recorded in transmission between 4000 and 400 $cm^{-1}$ on a Fourier transform device marketed by BRUCKER under reference VECTOR 22. The samples were prepared in the form of disks after dilution of approximately 1 mg of solid in 300 mg of KBr.

Catalytic Tests

Figure 1:
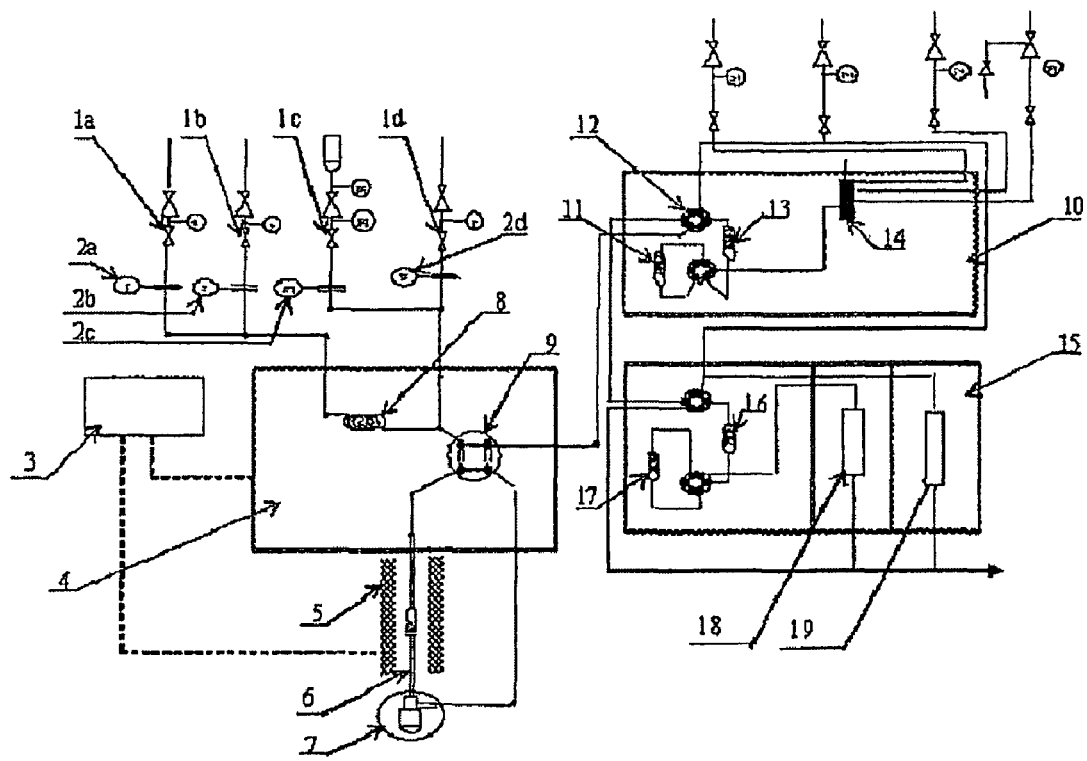
FIG. 1 is an apparatus shown in diagrammatic form, upon which the catalytic tests for the isobutane oxidation reaction were carried out.

The catalytic tests for the isobutane oxidation reaction were carried out on an apparatus as shown in diagrammatic form in FIG. 1.

The gases used (hydrogen, oxygen, isobutane, nitrogen) are distributed by the valves 1a, 1b, 1c and 1d, respectively, by means of mass flow meters 2a, 2b, 2c and 2d of the BROOK-FIELD type, permitting accurate regulation of the respective flow rates. The hot box 4 is maintained at 169° C. by a temperature-regulating system 3 associated with an oven 5, in order to avoid condensation in the pipes. The water is synthesized in the hot box 4 starting from oxygen and hydrogen on a catalyst 8 based on platinum supported on $Al_2O_3$. The hot box 4 is equipped with a four-way valve 9. A vertical fixed-bed reactor made of Pyrex 6 having a condensation system 7 is used. The catalyst is placed on a frit, and a glove finger (not shown) enables the temperature to be measured directly in the catalytic bed. This is the temperature that is recorded in all the tables of results. Typically, the weights of the catalysts tested are 2.0 g.

The condensation system 7 is fitted at the outlet of the reactor 6 in order to trap the condensable organic compounds. The trap containing an aqueous hydroquinone solution is maintained at 0° C. in ice. The non-condensable gases (CO, $CO_2$, $C_4H_{10}$, $C_4H_8$, $N_2$ and $O_2$) are analyzed in-line by chromatography after the trapping system.

The system of analysis is composed of two gas-phase chromatographs and a liquid-phase chromatograph. The first two, which are mounted in-line, permit analysis of the gases. The first chromatograph 10, which is equipped with a molecular sieve 11 (CP-MOLSIEVE® 5 Å), a packed column 13 (PO-RAPAK Q®) and a six-way valve 12, permits the separation and quantification of CO, $CO_2$, $N_2$ and $O_2$. The device is equipped with a detector 14, which is a catharometer, and the vector gas is helium. This system permits the detection of isobutane and isobutene, but not the separation thereof. A second chromatograph (not shown for reasons of simplicity) equipped with a packed column (Silica-Plot®) is used to effect the separation. Four analyses are carried out for each temperature, which represents a condensation time of about 120 minutes.

The condensable products (methacrylic and acetic acids, methacrolein, acetone and acrylic acid) are analyzed on a CHROMPACK 9001 chromatograph 15 equipped with a FID detector comprising a packed column 16 (Silica-Plot®) and a column 17 (CP-Sil®), and a CPWAX58/FF® column. The measuring system is shown diagrammatically at reference numeral 18, and the reference system is shown diagrammatically at reference numeral 19. The vector gas used is nitrogen. The injection is carried out by means of a CHROMPACK automatic sample changer of type CP9005. The volume injected is 0.5 ml and 5 injections per sample are effected. The measurement uncertainties are less than 2%.

The chromatogram obtained shows the characteristic peaks of methacrylic acid, acrylic acid, acetic acid and methacrolein.

The activities and selectivities were calculated taking into consideration the following reaction products: methacrylic acid (MAA), methacrolein (MA), acetic acid (AAc), acrylic acid (Acr), acetone (Ace), CO and $CO_2$.

A factor F was introduced into the conversion and selectivity calculations for internal calibration in order to eliminate errors due to dilution effects. This factor is determined by the ratio of the initial number of moles of nitrogen to the number of moles of nitrogen measured at the outlet of the reactor. The conversion of the reagent R (isobutane or oxygen) is therefore defined by the equation:

$$C(R) = \frac{N(R)_0 - N(R)F}{N(R)_0}$$

in which $N(R)_0$ is the number of moles of reagent R in the initial reaction mixture and $N(R)$ is the number of moles of reagent R at time t during the test.

The selectivity (S) of the different products is defined by the following equation:

$$S(P) = \frac{N(P)*nc(P)}{\sum N(P)*nc(P)}$$

in which $N(P)$ is the number of moles of product P at time t during the test, $nc(P)$ is the carbon (or oxygen) number in the molecule of product P.

The yield of product P($R(P)$) is defined by the equation:

$$R(P) = C(R) * S(P)$$

The carbon and oxygen balances were calculated for each analysis by measuring the quantities of products that had appeared and the conversions of reagents. These balances are produced taking into account the following equations:

$$C_4H_{10} + 2O_2 \rightarrow C_4H_5O_2 + 2H_2O$$

$$C_4H_{10} + 3/2 O_2 \rightarrow C_4H_5O + 2H_2O$$

$$C_4H_{10} + 5/2 O_2 \rightarrow 2C_2H_4O_2 + H_2O$$

$$3C_4H_{10} + 7/2 O_2 \rightarrow 4C_3H_6O + 3H_2O$$

$$3C_4H_{10} + 15/2 O_2 \rightarrow 4C_3H_4O_2 + 7H_2O$$

$$C_4H_{10} + 13/2 O_2 \rightarrow 4CO_2 + 5H_2O$$

$$C_4H_{10} + 9/2 O_2 \rightarrow 4CO + 5H_2O$$

The experimental conditions for the catalytic tests are as follows, unless indicated otherwise: two grams of catalyst are loaded into the reactor. The reaction temperature varies from 310 to 370° C. The total flow rate varies from 14 to 24 ml·min$^{-1}$. Since the measured density of the catalysts is 1.2, the contact time is typically of the order of 4.8 seconds for one gram of catalyst, that is to say an hourly volume velocity of 2600 h$^{-1}$. The catalysts were tested under standard supply conditions defined by the following ratios: $C_4H_{10}/O_2/H_2O/N_2 = 27/13.5/10/49.5$.

In order to ensure that no isobutane conversion took place without catalyst, the reactor was tested empty at 350° C. No isobutane conversion was observed at that temperature. The linear evolution of the isobutane conversion as a function of the flow rate of isobutane was also checked.

EXAMPLE 1

Compound of Formula $Cs_2Te_{0.3}V_{0.1}H_{0.2}PMo_{12}O_{40.4}/La_2Mo_2O_9$

Synthesis of the First Crystal Phase of Formula $Cs_2Te_{0.3}V_{0.1}H_{0.2}PMo_{12}O_{40.4}$.

Two solutions are prepared independently of one another.

The first solution is prepared by dissolving 8.16 g of phosphomolybdic acid (marketed by Fluka under reference 79560) and 0.18 g of telluric acid (marketed by Interchim under reference 014197) in 140 ml of water.

The second solution is prepared by dissolving 1.3 g of cesium carbonate (marketed by Interchim under reference 012887) in 0.4 ml of water.

The second solution is added to the first, with stirring. The precipitated solid is recovered in a rotary evaporator at 80° C., dried in an oven at 120° C. and calcined at 360° C. for 6 hours (temperature rise 5°·min$^{-1}$, air flow 50 ml·min$^{-1}$).

The resulting solid (6.5 g) is reacted with vanadium acetylacetonate ($V[C_5O_2H_7]_3$) (0.16 g) (marketed by Fluka under reference 1347-99-8) dissolved in toluene.

The progress of the reaction is monitored by the change in colour of the solution, which is coloured at the start and loses its colour when the vanadium has reacted with the solid which is not soluble. The reaction is complete after 10 to 12 hours under argon.

Characterization of the First Crystal Phase

The solid was characterized by chemical analysis. The atomic ratios Cs/Mo, P/Mo, Te/Mo and V/Mo were calculated starting from the results of the chemical analysis, and the specific surface area S was measured after catalytic testing. The results are shown in Table 2.

TABLE 2

| 2Cs/Mo | 12Te/Mo | 12P/Mo | 12V/Mo | S (m$^2$·g$^{-1}$) |
|---|---|---|---|---|
| 2 | 0.3 | 1.2 | 0.1 | 11.4 |

The calculated stoichiometries correspond to those desired.

The solid was also characterized by infra-red spectrometry after annealing under nitrogen at 360° C. The attribution of the bands is shown in Table 3.

TABLE 3

| | Characteristic bands | | | | |
|---|---|---|---|---|---|
| | $\delta(OH)$ | $v_a(P\text{---}O_a)$ | $v_a(Mo\text{---}O_d)$ | $v_a(Mo\text{---}O_b\text{---}Mo)$ | $v_a(Mo\text{---}O_c\text{---}Mo)$ |
| Frequency (cm$^{-1}$) | 1635 | 1063 | 970 | 868 | 803 |

The lines observed are characteristic of the anion having the Keggin structure of the formula $[PMo_{12}O_{40.4}]^-$. The indices a, b, c and d correspond to the oxygen atoms located at different positions in that anion. The anion is constituted by a central tetrahedron (P—$O_4$) surrounded by 12 $MoO_6$ octahedrons in four groups of three. The trimers, in which the octahedrons share edges, are linked with one another and with the central tetrahedron by vertices. The positions of the metal atoms are equivalent, whereas those of the oxygen atoms are not. Four types of oxygen atoms are distinguished: 4 oxygen atoms ($O_a$) common to the tetrahedron (P—$O_4$) and to three $MoO_6$ octahedrons sharing edges, 12 oxygen atoms ($O_b$) common to two octahedrons sharing a vertex, 12 oxygen atoms ($O_c$) common to two octahedrons sharing an edge, and 12 oxygen atoms ($O_d$) linked to a single metal atom by a double bond.

Figure 2:
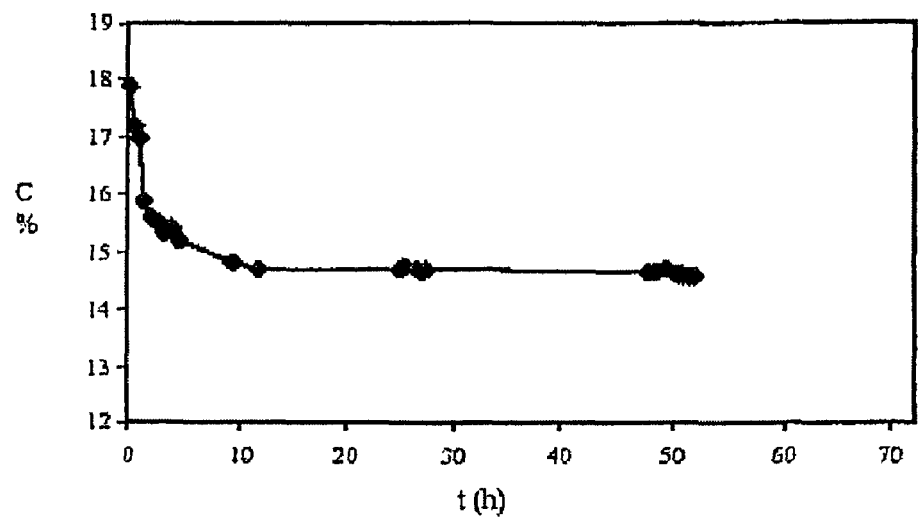
FIG. 2 shows the evolution of the conversion (C, %) over time (t, in hours) during the catalytic test at the reaction temperature of 350° C.

Catalytic Properties of the First Crystal Phase a) Evolution of the Catalytic Properties as a Function of the Reaction Time The evolution of the catalytic properties of the first crystal phase as a function of time was studied. FIG. 2 shows the evolution of the conversion (C, %) over time (t, in hours) during the catalytic test under the standard conditions defined above, at the reaction temperature of 350° C. A strong deactivation of the sample is observed at the start of the reaction, for about 5 hours, followed by stabilization. Measurements of the specific surface area before and after catalytic testing show that it diminished, changing from 28 to 11.8 $m^2 \cdot g^{-1}$.

b) Evolution of the Catalytic Properties as a Function of the Temperature

The catalytic performances of the sample are shown in Table 4 below, the tests having been conducted at three temperatures T: 330, 345 and 350° C.

TABLE 4

| T | Conversion | Selectivity (%) | | | | | Yield (%) |
|---|---|---|---|---|---|---|---|
| (° C.) | (%) | CO | CO$_2$ | AAc | MMA | MA | (MMA + MA) |
| 330 | 10.4 | 5 | 9 | 6 | 66 | 14 | 7.6 |
| 345 | 14.9 | 11 | 13 | 8 | 56 | 12 | 10.1 |
| 350 | 16.1 | 12 | 14 | 9 | 54 | 11 | 10.5 | c) Evolution of the Catalytic Properties as a Function of the Contact Time

Figure 3:
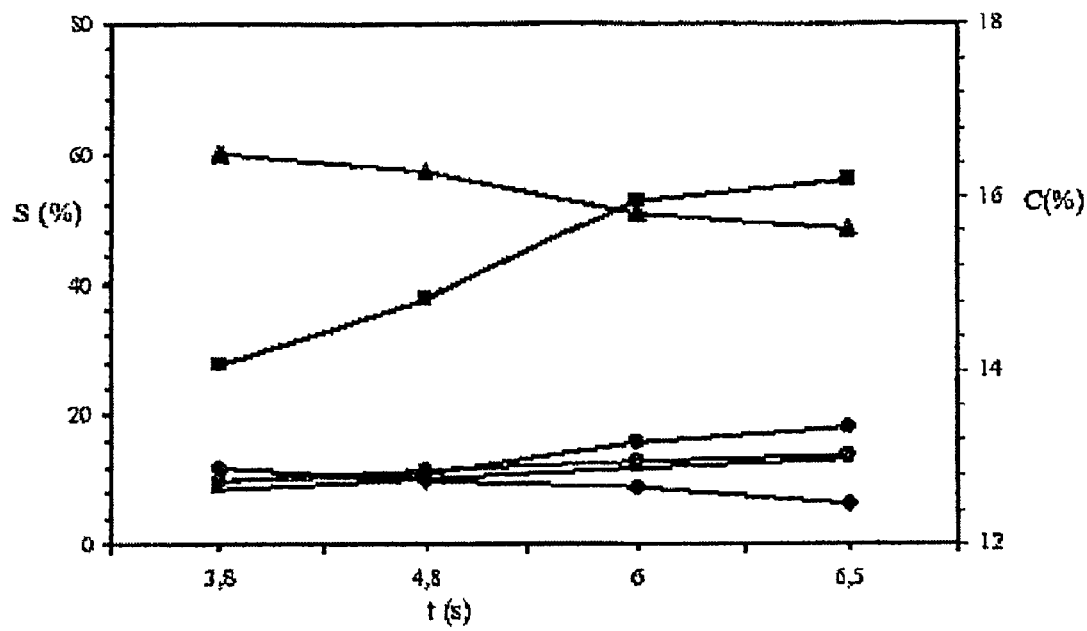
FIG. 3 shows the evolution of the selectivities (S, %) for methacrolein (♦), methacrylic acid (▲), acetic acid (●), CO (○) and $CO_2$ (◇) and the conversion (C, %) of isobutane (■) as a function of the contact time (t, in seconds).

The influence of the contact time on the catalytic properties of the sample was also studied, by modifying the flow rate of the reagents under standard test conditions, at 350° C. FIG. 3 shows the evolution of the selectivities (S, %) for methacrolein (♦), methacrylic acid (▲), acetic acid (●), CO (○) and CO$_2$ (◇) and the conversion (C, %) of isobutane (■) as a function of the contact time (t, in seconds). It is observed that increasing the contact time brings about an increase in the isobutane conversion and in the selectivities for CO, CO$_2$ and acetic acid, and a decrease in the selectivity for methacrolein and methacrylic acid.

d) Evolution of the Catalytic Properties as a Function of the Molar Ratio Isobutane/-Oxygen Because the composition of the batch plays a very important role in the oxidation reaction of isobutane to give methacrylic acid, the molar ratio isobutane/oxygen (iBu/O$_2$) was also chosen as a study parameter. The contact time was fixed at 4.8 seconds, the percentage of nitrogen and water at 49.5 and 10%, respectively, and the reaction temperature at 340° C. The results obtained are shown in Table 5.

TABLE 5

| Ratio | Conversion | Selectivity (%) | | | | | Yield (%) (MMA + |
|---|---|---|---|---|---|---|---|
| (iBu/O$_2$) | (%) | CO | CO$_2$ | AAc | MMA | MA | MA) |
| 1.4 | 15 | 13 | 15 | 9 | 54 | 8 | 9.5 |
| 1.7 | 13.3 | 12 | 15 | 7 | 59 | 7 | 8.8 |
| 2 | 12.5 | 8 | 13 | 8 | 62 | 9 | 8.9 |
| 3 | 11.2 | 8 | 11 | 6 | 64 | 10 | 8.4 |
| 3.5 | 10 | 6 | 9 | 7 | 65 | 13 | 7.8 | e) Evolution of the Catalytic Properties as a Function of the Nitrogen Partial Pressure The influence of the nitrogen partial pressure on the catalytic performances was also studied. The contact time was fixed at 4.8 seconds, the isobutane/oxygen ratio at 2 and the reaction temperature at 340° C. The catalytic results obtained are shown in Table 6.

TABLE 6

| N$_2$ | Conversion | Selectivity (%) | | | | | Yield (%) |
|---|---|---|---|---|---|---|---|
| (%) | (%) | CO | CO$_2$ | AAc | MMA | MA | (MMA + MA) |
| 71 | 15.9 | 5 | 5 | 11 | 67 | 13 | 12.7 |
| 55 | 11.6 | 8 | 12 | 7 | 67 | 6 | 8.5 |
| 49.5 | 12.5 | 8 | 13 | 8 | 62 | 9 | 9.1 |
| 44 | 10.4 | 9 | 16 | 7 | 62 | 6 | 7.1 |
| 36 | 12 | 9 | 15 | 13 | 50 | 13 | 7.6 | f) Characterization of the First Phase after Catalytic Testing

The first phase was characterized after catalytic testing by X-ray diffraction and infra-red spectroscopy. The diffractogram after testing is comparable with that before testing, showing that no profound modification has taken place. The results of characterization by infra-red spectroscopy are shown in Table 7.

TABLE 7

| | Characteristic bands | | | | |
|---|---|---|---|---|---|
| | $\delta(OH)$ | $v_a(P\text{---}O_a)$ | $v_a(Mo\text{---}O_d)$ | $v_a(Mo\text{---}O_b\text{---}Mo)$ | $v_a(Mo\text{---}O_c\text{---}Mo)$ |
| Frequency (cm$^{-1}$) | 1635 | 1063 | 970 | 867 | 800 |

The same lines are found as observed on the sample before catalytic testing is carried out.

Synthesis of the Second Crystal Phase of Formula $La_2Mo_2O_9$

This phase is prepared by reaction in the solid state between $MoO_3$ (marketed by Chempur under reference 005565) and $La_2O_3$ (marketed by Alfa Aesar under reference 011264). To that end, the reagents are weighed in stoichiometric proportions and ground in an agate mortar. The compound $La_2O_3$ has previously been heated to 1000° C. in order to avoid hydration thereof with time and the formation of $La(OH)_3$.

The mixture is then transferred to an aluminum boat. It is subjected to preheating at 500° C. and then to two successive annealing operations lasting 15 hours at a temperature of 960° C., between which the mixture is ground in acetone in order to homogenize it and ensure good dispersion of the grains, until the pure product is obtained. The purity of the product, in terms of phase composition, is checked by X-ray diffraction.

Characterization of the Second Crystal Phase

Figure 4:
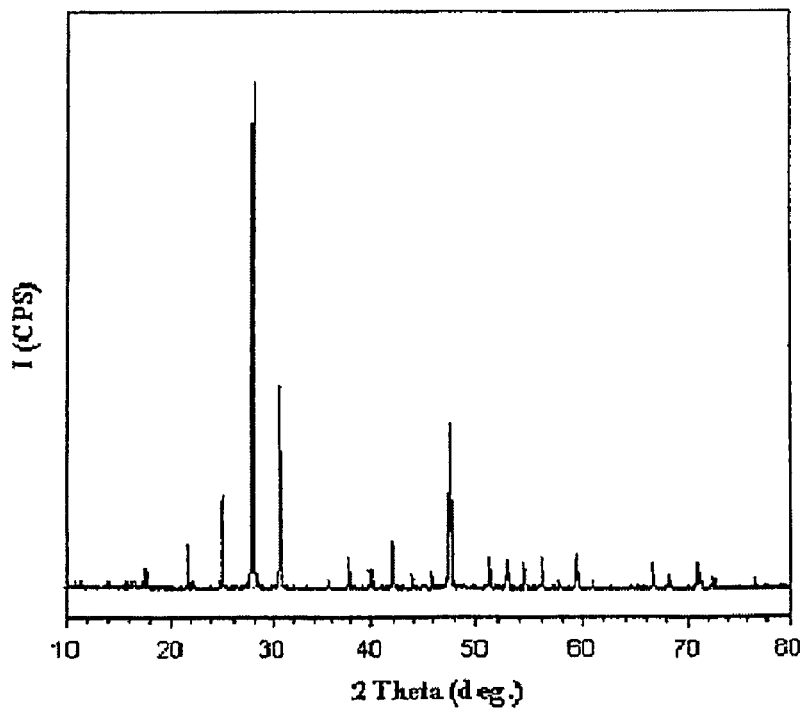
FIG. 4 is an X-ray diffractogram of the second phase, on which the intensity is indicated in counts per second (CPS).

The second phase was characterized by X-ray diffraction. The diffractogram of the second phase, on which the intensity is indicated in counts per second (CPS) (FIG. 4), corresponds to that of the cubic phase of lanthanum molybdate.

Catalytic Properties of the Second Crystal Phase

The catalytic performances of the second crystal phase are shown in Table 8 below, the test having been conducted at a temperature of 360° C. using the reaction mixture isobutane/$O_2/H_2O/N_2$=27/13.5/10.0/49.5 and a contact time of 4.8 seconds.

TABLE 8

| Conversion (%) | Selectivity (%) | | | | | Yield (%) (MMA + MA) |
|---|---|---|---|---|---|---|---|
| | CO | $CO_2$ | AAc | MMA | MA | Isobutene | |
| 1.7 | 9.1 | 7.7 | Trace | — | — | 83.4 | — |

Preparation of the Final Compound

The final compound is prepared by mixing the first and second phases by simple mechanical grinding.

Various tests were carried out, the respective proportions of the two phases being varied. The composition and the numbers attributed to the samples corresponding to these tests are compiled in Table 9.

TABLE 9

| Name of sample | Percentage by weight of first phase | Percentage by weight of second phase |
|---|---|---|
| Compound 1a | 80 | 20 |
| Compound 1b | 70 | 30 |
| Compound 1c | 50 | 50 |

Catalytic Properties of the Final Compound

The catalytic properties of compounds 1a, 1b and 1c were tested under a number of experimental conditions.

Figure 5A:
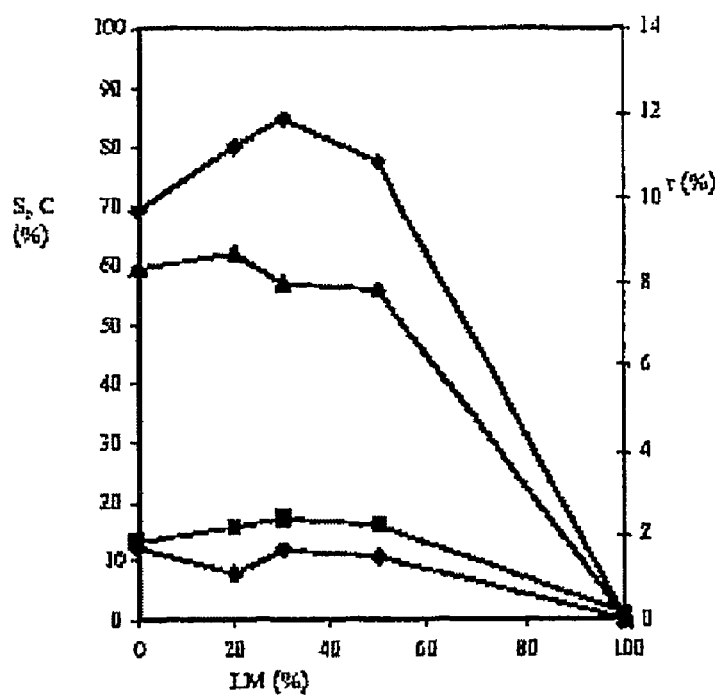
FIGS. 5a and 5b show the evolution of the conversion C (in %) of isobutane (■), of the selectivities (in %) for MMA (▲) and MA (♦) and of the yield r of MMA and MA (◇) at 345° C.
Figure 5B:
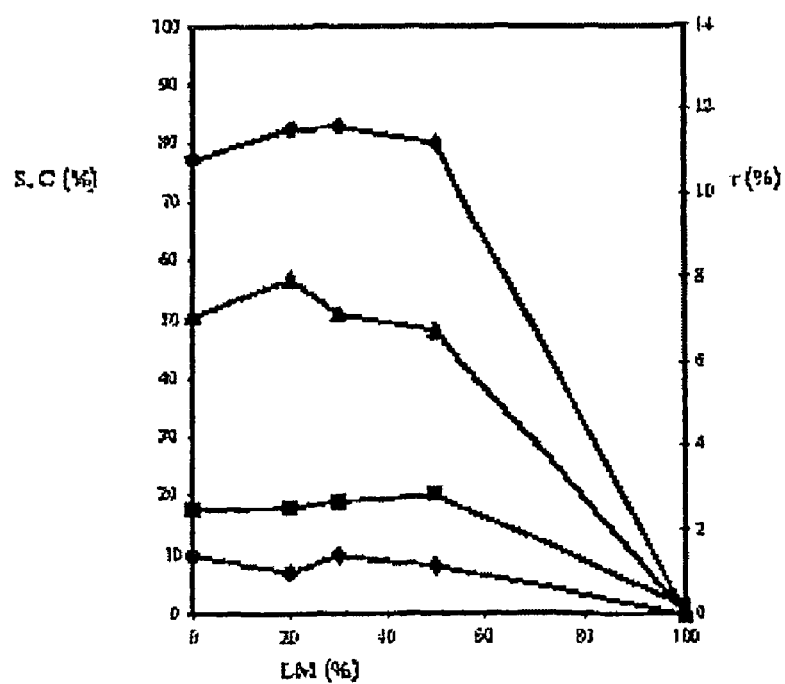

The results obtained are compiled in Table 10 and in FIGS. 5a and 5b, which show the evolution of the conversion C (in %) of isobutane (□), of the selectivities (in %) for MMA (▲) and MA (♦) and of the yield r of MMA and MA (◇) at 345° C. (FIG. 5a) and 369° C. (FIG. 5b) as a function of the content by weight of lanthanum molybdate (denoted LM, in %). Each compound was tested under the standard conditions and at three different temperatures.

TABLE 10

| Compound | T (° C.) | Conversion (%) | Selectivity (%) | | | | | Yield (%) (MMA + MA) |
|---|---|---|---|---|---|---|---|---|
| | | | CO | $CO_2$ | AAc | MMA | MA | |
| 1a | 312 | 10 | 3 | 8 | 4 | 77 | 8 | 8.5 |
| | 345 | 16 | 9 | 12 | 9 | 62 | 8 | 11.2 |
| | 369 | 18 | 13 | 15 | 8 | 57 | 7 | 11.5 |
| 1b | 312 | 11 | 6 | 4 | 7 | 69 | 14 | 9.1 |
| | 345 | 17.2 | 11 | 10 | 12 | 57 | 12 | 11.7 |
| | 369 | 19 | 15 | 13 | 11 | 51 | 10 | 11.6 |
| 1c | 315 | 11.1 | 5 | 3 | 6 | 72 | 13 | 9.4 |
| | 358 | 18.5 | 12 | 13 | 13 | 50 | 11 | 11.3 |
| | 368 | 20 | 16 | 16 | 11 | 48 | 8 | 11.2 |

An increase in the selectivity for methacrylic acid is noted at low temperature, with a maximum at about 30% lanthanum molybdate. The activity observed therefore does not correspond to the sum of the activities of the pure phases and a synergy effect between phases has taken place. The yield of methacrylic acid and methacrolein only falls by about 1% when the mixture contains 50% by weight lanthanum molybdate.

The conditions for the catalytic testing of the mixture with 20% molybdate (compound 1a) were modified by choosing a reaction medium that is richer in oxygen. The temperature is 360° C. and the contact time is 4.8 seconds. The results obtained are shown in Table 11.

TABLE 11

| $C_4H_{10}/$ $O_2/H_2O/N_2$ | Conversion (%) | Selectivity (%) | | | | | Yield (%) MMA + MA |
|---|---|---|---|---|---|---|---|
| | | CO | $CO_2$ | AAc | MMA | MA | |
| 27/27/10/36 | 22 | 17 | 17 | 10 | 51 | 6 | 12.5 |
| 27/13.5/10/49.5 | 17 | 12 | 14 | 9 | 59 | 7 | 11.2 |

The conversion increases without any great fall in selectivity. There is thus obtained a conversion of 22% with a selectivity for methacrylic acid and methacrolein of 57% and a productivity which reaches 78 ($g_{MMA}$, $kg^{-1}$ catalyst·$h^{-1}$).

Figure 6:
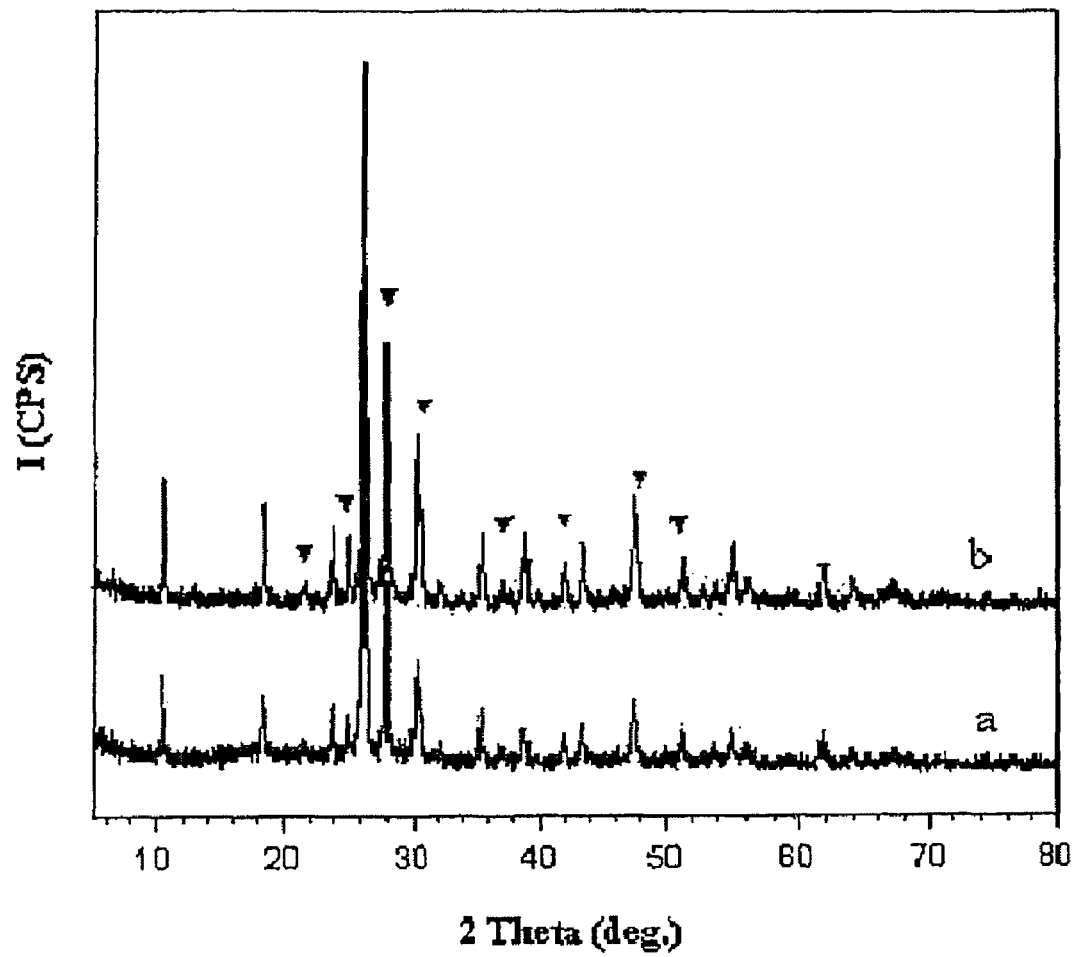
FIG. 6 shows X-ray diffractograms of a compound before catalytic testing (diffractogram a) and after catalytic testing (diffractogram b).

The X-ray diffractograms of compound 1c before catalytic testing (diffractogram a) and after catalytic testing (diffractogram b) are shown in FIG. 6 (the intensity is given in counts per second (CPS)). The marks (▼) represent the peaks corresponding to the second crystal phase $La_2Mo_2O_9$. These diffractograms do not show any phase conversion.

EXAMPLE 2

Preparation of a Compound of the Formula $Cs_2Te_{0.3}V_{0.1}H_{0.2}PMo_{12}O_{40.4}/La_2Mo_{1.9}V_{0.1}O_{8.95}$ This compound is constituted by a first phase identical with that of Example 1 and a different second phase.

Synthesis of the First Crystal Phase of the Formula $Cs_2Te_{0.3}V_{0.1}H_{0.2}PMo_{12}O_{40.4}$.

The first crystal phase was prepared using the same experimental conditions as for the first phase of Example 1.

Synthesis of the Second Crystal Phase of the Formula $La_2Mo_{1.9}V_{0.1}O_{8.95}$ The second crystal phase was synthesized under experimental conditions similar to those described for the second phase of Example 1, except that the compound $V_2O_5$ (marketed by Alfa Aesar under reference 81110) was added to $MoO_3$ and $La_2O_3$ in stoichiometric proportions and that, after preheating, the mixture was subjected to 7 successive annealing operations lasting 15 hours at a temperature of 925° C.

Characterization of the Second Crystal Phase

Figure 7:
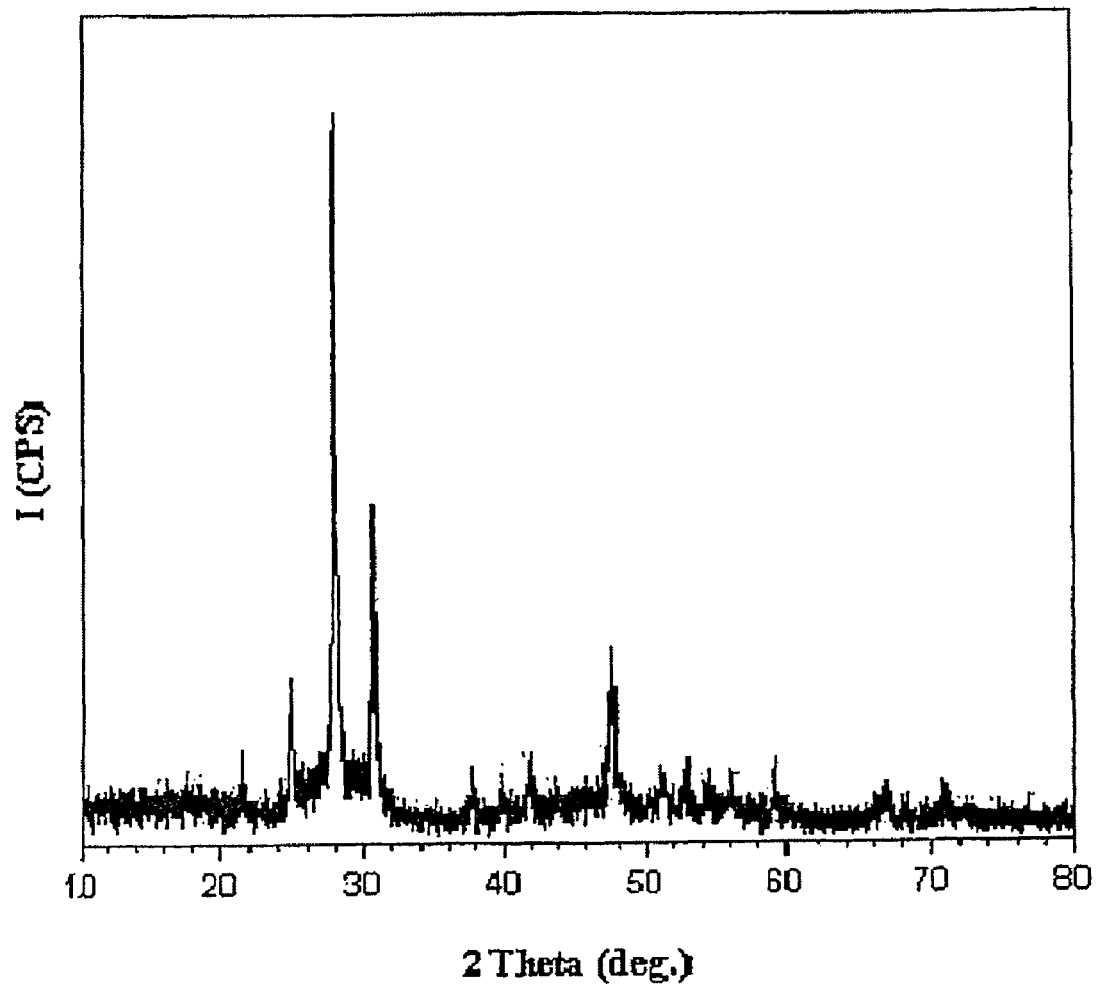
FIG. 7 shows an X-ray diffractogram of the second crystal phase synthesized under experimental conditions similar to those described for the second phase of Example 1.

The second phase was characterized by X-ray diffraction. The diffractogram of the second phase (FIG. 7, in which the intensity I is indicated in counts per second), corresponds to that of the cubic phase of lanthanum molybdate.

Catalytic Properties of the Second Crystal Phase

The catalytic performances of the second crystal phase are shown in Table 12 below, the tests having been conducted at a temperature of 360° C. with a contact time of 6 seconds, with variation of the supply conditions (defined by the ratios $C_4H_{10}/O_2/H_2O/N_2$).

TABLE 12

| $C_4H_{10}/$ $O_2/H_2O/N_2$ | Conversion (%) | Selectivity (%) | | | | |
|---|---|---|---|---|---|---|
| | | CO | $CO_2$ | AAc | MMA | MA | isobutene |
| 40/20/10/30 | 3 | 3 | 2 | — | — | 6 | 88 |
| 10/10/10/70 | 3.5 | 1 | 1 | — | — | — | 98 |

Preparation of the Final Compound

The final compound is prepared by mixing the first and second phases by simple mechanical grinding.

Various tests were carried out, the respective proportions of the two phases being varied. The composition and the numbers attributed to the samples corresponding to these tests are compiled in Table 13.

TABLE 13

| Name of sample | Percentage by weight of first phase | Percentage by weight of second phase |
|---|---|---|
| Compound 2a | 70 | 30 |
| Compound 2b | 50 | 50 |
| Compound 2c | 30 | 70 |

Catalytic Properties of the Final Compound

The results obtained under various reaction conditions for compounds 2a and 2b are compiled in Table 14.

TABLE 14

| | | Reaction conditions | | | Selectivity (%) | | | | |
|---|---|---|---|---|---|---|---|---|---|
| Catalyst | $iBu/O_2/H_2O/N_2$ | T (° C.) | Contact time (s) | Conversion (%) | CO | $CO_2$ | AAc | MMA | MA |
| 2a | 10/10/10/70 | 360 | 6 | 25 | 16 | 16 | 12 | 48 | 4 |
| 2b | 10/10/10/70 | 360 | 6 | 21 | 17 | 13 | 11 | 58 | 1 |
| 2c | 10/10/10/70 | 360 | 6 | 19.6 | 25 | 22 | 8 | 38 | 5 |
| 2b | 40/20/10/30 | 360 | 6 | 16 | 8 | 11 | 6 | 72 | 3 |
| 2b | 27/27/10/36 | 350 | 6 | 21.9 | 15.8 | 9 | 12 | 60 | 3 |
| 2b | 21.6/37.8/10/30.6 | 350 | 6 | 26 | 12 | 10 | 16 | 61 | 3 |
| 2b | 11.7/19.8/10/58.5 | 350 | 3 | 17.5 | 5 | 6 | 13 | 70 | 5 |

As compared with compounds 1a, 1b and 1c, it appears that the catalysts obtained have both a greater activity and a greater selectivity for MMA. The maximum activity is observed for mixtures that are rich in first crystal phase (compound 2a), while optimum selectivity is obtained for compound 2b (50% first crystal phase/50% second crystal phase).

Evolution of the Catalytic Properties as a Function of the Content of $CO_2$

The catalytic performances of the compound according to Example 2 ($Cs_2Te_{0.3}V_{0.1}H_{0.2}PMo_{12}O_{40.4}$/$La_2Mo_{1.9}V_{0.1}O_{8.95}$) are shown in Table 15 below and summarized in FIG. 8.

Figure 8:
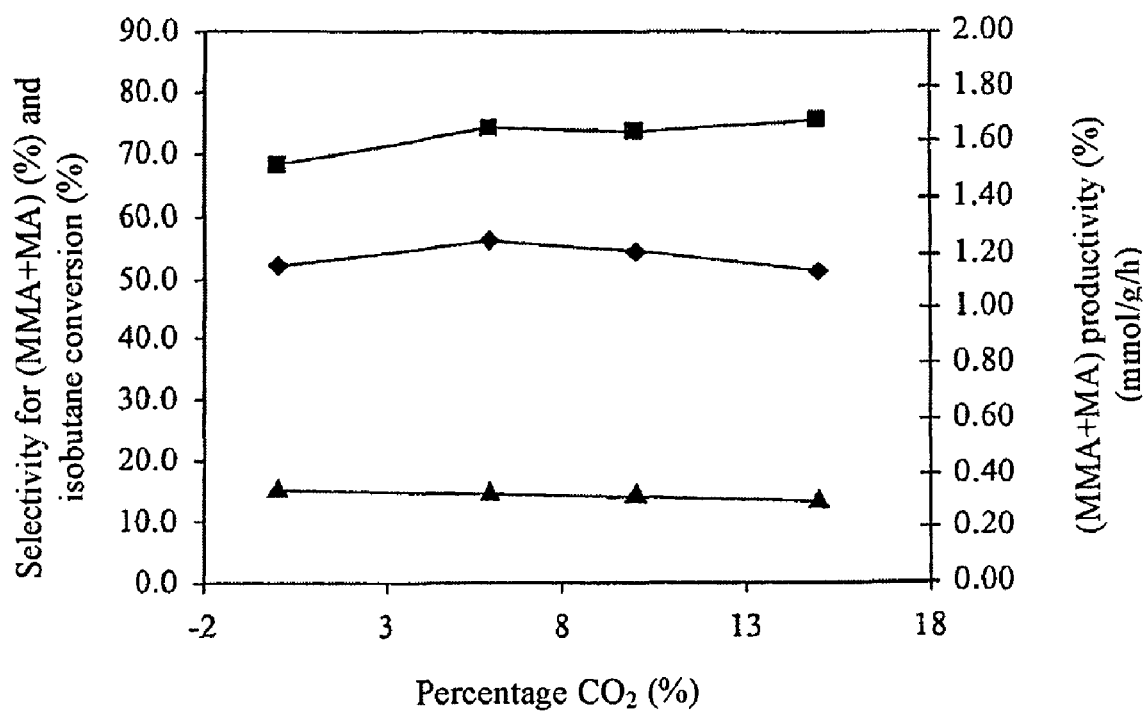
FIG. 8 shows the evolution of the productivity of (MMA+MA) (♦), of the selectivity for (MMA+MA) (■), and of the isobutane conversion (▲) as a function of the amount of $CO_2$ in the reaction mixture.

FIG. 8 shows the evolution of the productivity of (MMA+MA) (♦), of the selectivity for (MMA+MA) (■) and of the isobutane conversion (▲) as a function of the amount of $CO_2$ in the reaction mixture.

The tests were conducted for a compound $Cs_2Te_{0.3}V_{0.1}H_{0.2}PMo_{12}O_{40.4}$/$La_2Mo_{1.9}V_{0.1}O_{8.95}$ having a ratio by weight of 50/50 between the first and second crystal phases, a mass of catalyst of 1.45 g, a contact time of 4.8 seconds, a temperature of 345° C. The ratio by volume of $iC_4H_{10}/O_2/H_2O/N_2/CO_2$ is 40/20/10/58.5/X, where X represents the percentage of $CO_2$ indicated in Table 15 below.

TABLE 15

| Percentage $CO_2$ (%) | Conversion (%) | Selectivity (%) | | | | | Carbon balance | Productivity (mmol·g$^{-1}$·h$^{-1}$) (MMA + MA) |
|---|---|---|---|---|---|---|---|---|
| | | CO | $CO_2$ | AAc | MMA | MA | | |
| 0 | 15.4 | 10 | 12 | 8 | 65 | 3 | 100 | 1.16 |
| 6 | 15.2 | 9 | 11 | 7 | 69 | 5 | 99 | 1.25 |
| 10 | 14.8 | 10 | 10 | 6 | 70 | 4 | 99 | 1.21 |
| 15 | 13.6 | 10 | 9 | 6 | 71 | 4 | 100 | 1.14 |

An increase in the selectivity for (MMA+MA), given by the sum of the selectivities for MMA and MA, respectively, is observed when the $CO_2$ content in the reaction mixture increases.

Evolution of the Catalytic Properties as a Function of the Total Pressure

The catalytic performances of the compound $Cs_2Te_{0.3}V_{0.1}H_{0.2}PMo_{12}O_{40.4}/La_2Mo_{1.9}V_{0.1}O_{8.95}$ according to Example 2 are shown in Table 16 below. The total pressure corresponds to the total pressure exerted on the reaction medium.

The tests were carried out for a compound $Cs_2Te_{0.3}V_{0.1}H_{0.2}PMo_{12}O_{40.4}/La_2Mo_{1.9}V_{0.1}O_{8.95}$ having a ratio by weight of 50/50 between the first and second crystal phases.

Two supply conditions (SC) are used:
a: $iC_4H_{10}/O_2/H_2O/N_2 = 27/13.5/10/49.5$;
b: $iC_4H_{10}/O_2/H_2O/N_2 = 40/20/10/30$.

TABLE 16

| SC | Temperature (K) | SV (ml·g$^{-1}$·h$^{-1}$) | $P_{total}$ (kPa) | $P_{i\text{-}C4H10}$ (kPa) | Contact time (s) | Conversion (%) | Selectivity MMA + MA | Productivity (mmol·g$^{-1}_{cata}$·h$^{-1}$) |
|---|---|---|---|---|---|---|---|---|
| a | 588 | 540 | 100 | 27 | 4.8 | 11.1 | 85 | 0.6 |
| b | 633 | 540 | 100 | 40 | 6 | 16 | 75 | 1.1 |
| b | 590 | 3000 | 160 | 59.2 | 1.1 | 5.6 | 87 | 2.6 |

These results show that an increase in the total pressure induces a net increase in both the MMA+MA selectivity and the productivity.

The invention claimed is:

1. A compound comprising a combination of a first and a second crystal phase, the first crystal phase being of the phosphomolybdic type, wherein the first crystal phase corresponds to formula (1):

$$A_aE_bV_cMo_dP_eO_fH_g \quad (1)$$

in which:
A is an alkali metal;
E represents tellurium;
the indices a, b, c, d, e, g are such that: $0 \leq a \leq 3$, $0 < b \leq 3$, $0 \leq c \leq 3$, $0 < d \leq 13$, $0 < e \leq 2$, $0 \leq g \leq 3$, and f represents the number of oxygen atoms necessary to satisfy the valence and the relative atomic proportions of the elements that are present,
and the second crystal phase corresponds to formula (2):

$$Z_gMo_hX_iO_j \quad (2)$$

in which:
Z is selected from the trivalent rare earths;
X is selected from the elements V, Ga, Fe, Bi, Ce, Ti, Sb, Mn, Zn, Te;
the indices g, h and i are such that: $0 < g \leq 3$, $0 \leq h \leq 3$, $0 \leq i \leq 1$, and j represents the number of oxygen atoms necessary to satisfy the valence and the relative atomic proportions of the elements that are present.

2. The compound as claimed in claim 1, wherein A represents cesium.

3. The compound as claimed in claim 1, wherein X is V, Ga, Fe, Bi, Ce, Ti, Mn, Zn, Te.

4. The compound as claimed in claim 1, wherein the proportion of the second crystal phase is less than or equal to 50% by weight, based on the weight of the compound.

5. The compound as claimed in claim 1, wherein the first crystal phase corresponds to the formula $Cs_2Te_{0.3}V_{0.1}H_{0.2}PMo_{12}O_{40.4}$.

6. The compound as claimed in claim 1, wherein the second crystal phase corresponds to the formula $La_2Mo_2O_9$.

7. The compound as claimed in claim 1, wherein the second crystal phase corresponds to the formula $La_2Mo_{1.9}V_{0.1}O_{8.95}$.

8. The compound as claimed in claim 1, wherein it is formed by a combination of a first crystal phase of the formula $Cs_2Te_{0.3}V_{0.1}H_{0.2}PMo_{12}O_{40.4}$ and a second crystal phase of the formula $La_2Mo_2O_9$.

9. The compound as claimed in claim 1, wherein it is formed by a combination of a first crystal phase of the formula $Cs_2Te_{0.3}V_{0.1}H_{0.2}PMo_{12}O_{40.4}$ and a second crystal phase of the formula $La_2Mo_{1.9}V_{0.1}O_{8.95}$.

10. A process for the preparation of a compound as claimed in claim 1, which comprises the following steps:
synthesis of the first crystal phase in the form of a first powder;
synthesis of the second crystal phase in the form of a second powder;
mixing of said first and second powders by grinding.

11. A catalyst for the oxidation of alkanes, comprising the compound of claim 1.

12. A method for the oxidation of alkanes, comprising a step of passing a gaseous mixture comprising said alkanes, and optionally an inert gas and/or molecular oxygen, over the compound of claim 1.

13. A catalyst for the oxidation of isobutane to give methacrylic acid and methacrolein, comprising the compound of claim 1.

14. A method for oxidation of isobutene to give methacrylic acid and methacrolein, comprising a step of passing a gaseous mixture comprising isobutene, and optionally an inert gas and/or molecular oxygen, over the compound according to claim 1.

15. A catalyst for the oxidation of isobutene and methacrolein to give methacrylic acid, comprising the compound of claim 1.

16. A method for oxidation of isobutene and methacrolein to give methacrylic acid, comprising a step of passing a gaseous mixture comprising isobutene and methacrolein, and optionally an inert gas and/or molecular oxygen, over the compound according to claim 1.

17. A compound comprising a combination of a first and a second crystal phase, the first crystal phase being of the phosphomolybdic type, wherein the first crystal phase corresponds to formula (1):

$$A_a E_b V_c Mo_d P_e O_f H_g \qquad (1)$$

in which:
A is an alkali metal;
E is selected from the elements Te, Sb and Bi;
the indices a, b, c, d, e, g are such that: $0 \leq a \leq 3$, $0 < b \leq 3$, $0 \leq c \leq 3$, $0 < d \leq 13$, $0 < e \leq 2$, $0 \leq g \leq 3$, and f represents the number of oxygen atoms necessary to satisfy the valence and the relative atomic proportions of the elements that are present, and the second crystal phase corresponds to formula (2):

$$Z_g Mo_h X_i O_j \qquad (2)$$

in which:
Z is selected from the trivalent rare earths;
X is selected from the elements V, Ga, Fe, Bi, Ce, Ti, Sb, Mn, Zn, Te;
the indices g, h and i are such that: $0 < g \leq 3$, $0 \leq h \leq 3$, $0 \leq i \leq 1$, and j represents the number of oxygen atoms necessary to satisfy the valence and the relative atomic proportions of the elements that are present,
wherein Z represents lanthanum.

18. A method for the oxidation of alkanes, comprising a step of passing a gaseous mixture comprising said alkanes, and optionally an inert gas and/or molecular oxygen, over the compound of claim 17.

19. A compound comprising a combination of a first and a second crystal phase, the first crystal phase being of the phosphomolybdic type, wherein the first crystal phase corresponds to formula (1):

$$A_a E_b V_c Mo_d P_e O_f H_g \qquad (1)$$

in which:
A is an alkali metal;
E is selected from the elements Te, Sb and Bi;
the indices a, b, c, d, e, g are such that: $0 \leq a \leq 3$, $0 < b \leq 3$, $0 \leq c \leq 3$, $0 < d \leq 13$, $0 < e \leq 2$, $0 \leq g \leq 3$, and f represents the en atoms necessary to satisfy the valence and the relative atomic proportions of the elements that are present, and the second crystal phase corresponds to formula (2):

$$Z_g Mo_h X_i O_j \qquad (2)$$

in which:
Z is selected from the trivalent rare earths;
X is selected from the elements V, Ga, Fe, Bi, Ce, Ti, Sb, Mn, Zn, Te;
the indices g, h and i are such that: $0 < g \leq 3$, $0 \leq h \leq 3$, $0 \leq i \leq 1$, and j represents the number of oxygen atoms necessary to satisfy the valence and the relative atomic proportions of the elements that are present,
wherein X represents vanadium.

20. A method for the oxidation of alkanes, comprising a step of passing a gaseous mixture comprising said alkanes, and optionally an inert gas and/or molecular oxygen, over the compound of claim 19.

21. A process for the preparation of a compound comprising a combination of a first and a second crystal phase, the first crystal phase being of the phosphomolybdic type, wherein the first crystal phase corresponds to formula (1):

$$A_a E_b V_c Mo_d P_e O_f H_g \qquad (1)$$

in which:
A is an alkali metal;
E is selected from Te, Sb and Bi;
the indices a, b, c, d, e, g are such that: $0 \leq a \leq 3$, $0 < b \leq 3$, $0 \leq c \leq 3$, $0 < d \leq 13$, $0 < e \leq 2$, $0 \leq g \leq 3$, and f represents the number of oxygen atoms necessary to satisfy the valence and the relative atomic proportions of the elements that are present, and the second crystal phase corresponds to formula (2):

$$Z_g Mo_h X_i O_j \qquad (2)$$

in which:
Z is selected from the trivalent rare earths;
X is selected from the elements V, Ga, Fe, Bi, Ce, Ti, Sb, Mn, Zn, Te;
the indices g, h and i are such that: $0 < g \leq 3$, $0 \leq h \leq 3$, $0 \leq i \leq 1$, and j represents the number of oxygen atoms necessary to satisfy the valence and the relative atomic proportions of the elements that are present,
which comprises the following steps:
  synthesis of the first crystal phase in the form of a first powder;
  synthesis of the second crystal phase in the form of a second powder;
  mixing of said first and second powders by grinding
wherein the synthesis of the first crystal phase comprises the following successive steps:
  preparation of an aqueous solution comprising phosphomolybdic acid and a compound of the element E;
  mixing of said aqueous solution with an aqueous solution comprising a salt of the element A;
  precipitation, drying and calcination of said mixture in order to obtain a solid phase;
  mixing of said solid with a toluene solution comprising a compound of vanadium;
  filtration and drying at ambient temperature.

22. The process as claimed in claim 21, wherein the compound of the element E is selected from the group consisting of an acid, a chloride or an alkoxide, the salt of the element A is selected from the group consisting of a carbonate or a nitrate, and the compound of vanadium is selected from the group consisting of vanadium oxide or vanadium acetylacetonate.

23. A process, for the preparation of a compound comprising a combination of a first and a second crystal phase, the first crystal phase being of the phosphomolybdic type, wherein the first crystal phase corresponds to formula (1):

$$A_a E_b V_c Mo_d P_e O_f H_g \qquad (1)$$

in which:
A is an alkali metal;
E is selected from the elements Te, Sb and Bi;
the indices a, b, c, d, e, g are such that: $0 \leq a \leq 3$, $0 < b \leq 3$, $0 \leq c \leq 3$, $0 < d \leq 13$, $0 < e \leq 2$, $0 \leq g \leq 3$, and f represents the number of oxygen atoms necessary to satisfy the valence and the relative atomic proportions of the elements that are present, and the second crystal phase corresponds to formula (2):

$$Z_g Mo_h X_i O_j \quad (2)$$

in which:
Z is selected from the trivalent rare earths;
X is selected from the elements V, Ga, Fe, Bi, Ce, Ti, Sb, Mn, Zn, Te;
the indices g, h and i are such that: $0 < g \leq 3$, $0 \leq h \leq 3$, $0 \leq i \leq 1$, and j represents the number of oxygen atoms necessary to satisfy the valence and the relative atomic proportions of the elements that are present,
which comprises the following steps:
    synthesis of the first crystal phase in the form of a first powder;
    synthesis of the second crystal phase in the form of a second powder;
    mixing of said first and second powders by grinding wherein the synthesis of the second crystal phases comprises the following successive steps:
    mixing, by grinding, of molybdenum oxide $MoO_3$ in the solid state and an oxide of the element Z in the solid state;
    heating of said mixture to a temperature of the order of 500° C.;
    carrying out successive operations of annealing said mixture at a temperature greater than 500° C. until the end product is obtained in powder form.

24. The process as claimed in claim 23, wherein a compound of the element X replaces part of the molybdenum oxide.

25. The process as claimed in claim 24, wherein the compound of the element X is selected from the group consisting of a vanadium oxide or ammonium vanadate.

* * * * *